(12) United States Patent
Creedon et al.

(10) Patent No.: US 9,662,195 B2
(45) Date of Patent: May 30, 2017

(54) IMPLANT DEVICE FOR USE IN SALIVARY GLAND DUCT

(71) Applicant: E. Benson Hood Laboratories, Pembroke, MA (US)

(72) Inventors: Dennis Creedon, Sandwich, MA (US); Lewis H Marten, Westwood, MA (US); Christopher Vettori, Marshfield, MA (US); Rohan R Walvekar, Metairie, LA (US)

(73) Assignee: E. BENSON HOOD LABORATORIES, Pembroke, MA (US)

( * ) Notice: Subject to any disclaimer, the term of this patent is extended or adjusted under 35 U.S.C. 154(b) by 402 days.

(21) Appl. No.: 13/907,346

(22) Filed: May 31, 2013

(65) Prior Publication Data

US 2013/0268086 A1  Oct. 10, 2013

Related U.S. Application Data

(63) Continuation-in-part of application No. 13/180,187, filed on Jul. 11, 2011, now Pat. No. 8,517,971.

(60) Provisional application No. 61/362,985, filed on Jul. 9, 2010, provisional application No. 61/423,968, filed on Dec. 16, 2010, provisional application No. 61/653,825, filed on May 31, 2012.

(51) Int. Cl.
*A61M 25/00* (2006.01)
*A61F 2/04* (2013.01)

(52) U.S. Cl.
CPC ............... *A61F 2/04* (2013.01); *A61M 25/00* (2013.01)

(58) Field of Classification Search
CPC .......... A61F 2/04; A61M 24/00; A61M 25/00
See application file for complete search history.

(56) References Cited

U.S. PATENT DOCUMENTS

| | | | | |
|---|---|---|---|---|
| 4,981,475 A | * | 1/1991 | Haindl | A61M 25/02 128/DIG. 26 |
| 5,171,216 A | * | 12/1992 | Dasse | A61M 25/007 604/175 |
| 5,382,239 A | * | 1/1995 | Orr | A61M 25/02 604/177 |
| 6,110,185 A | | 8/2000 | Barra et al. | |

(Continued)

OTHER PUBLICATIONS

Buckenham, M.D., Tim: "Salivary Duct Intervention", *Seminars in Interventional Radiology*, vol. 21, No. 3, 2004, pp. 143-148.

(Continued)

*Primary Examiner* — Leslie Deak
*Assistant Examiner* — Kai Weng
(74) *Attorney, Agent, or Firm* — Wissing Miller LLP

(57) ABSTRACT

An implant device for placement within a salivary gland duct having a first end adjacent a parotid gland and a second end adjacent a submandibular gland. The implant device comprises an elongate body having a lumen, and a first and a second plate offset from the proximal end of the elongate body. The first plate is located on one side of the elongate body and the second plate is located on the other side of the elongate body. The first plate includes a first and a second hole operable to suture the first plate to a location adjacent the parotid gland. The second plate includes a first and a second hole operable to suture the second plate to a location adjacent the submandibular gland.

20 Claims, 12 Drawing Sheets

(56) References Cited

U.S. PATENT DOCUMENTS

2006/0025723 A1\* 2/2006 Ballarini ........................ 604/180
2007/0162148 A1 7/2007 Nahlieli
2007/0212393 A1\* 9/2007 Patravale et al. ............. 424/423

OTHER PUBLICATIONS

Aslam, M.O. et al.: "Technical Report: Wire Guided Sialography", *Clinical Radiology*, vol. 44, Issue 5, 1991, pp. 350-351.

\* cited by examiner

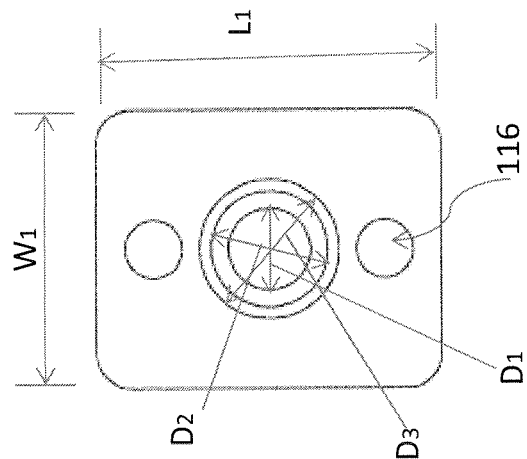
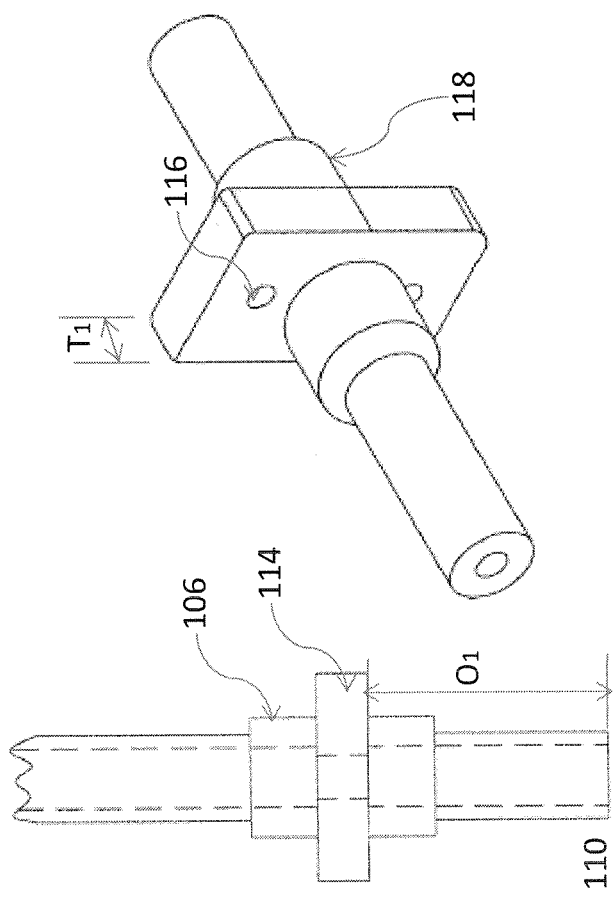
FIG. 2A　　FIG. 2B　　FIG. 2C

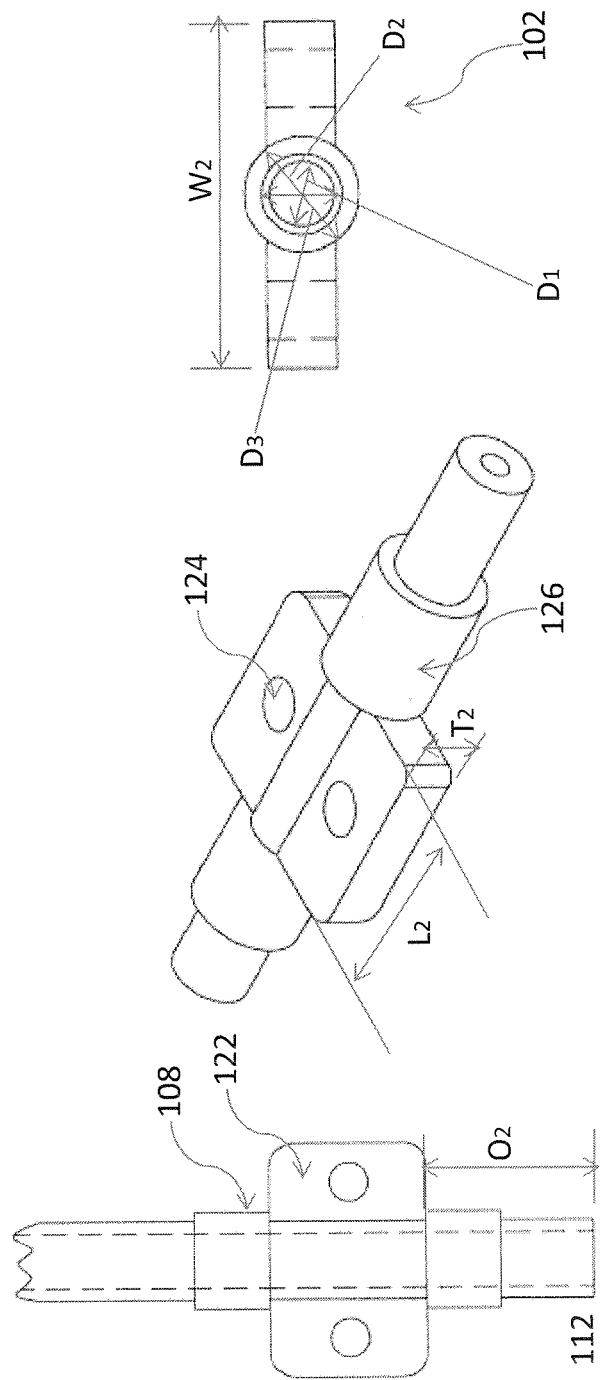

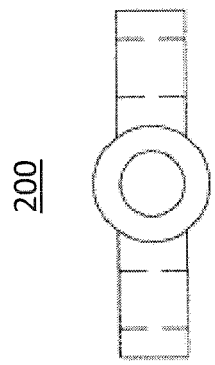
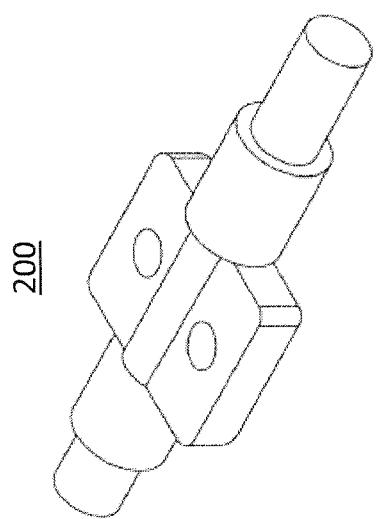
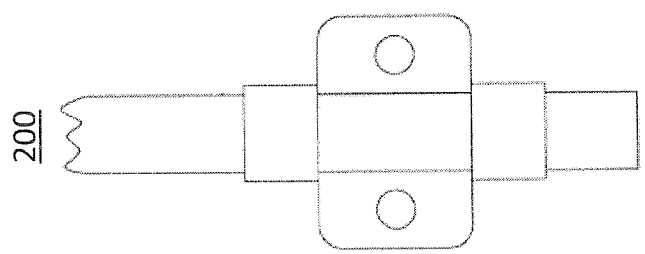
FIG. 6C
FIG. 6B
FIG. 6A

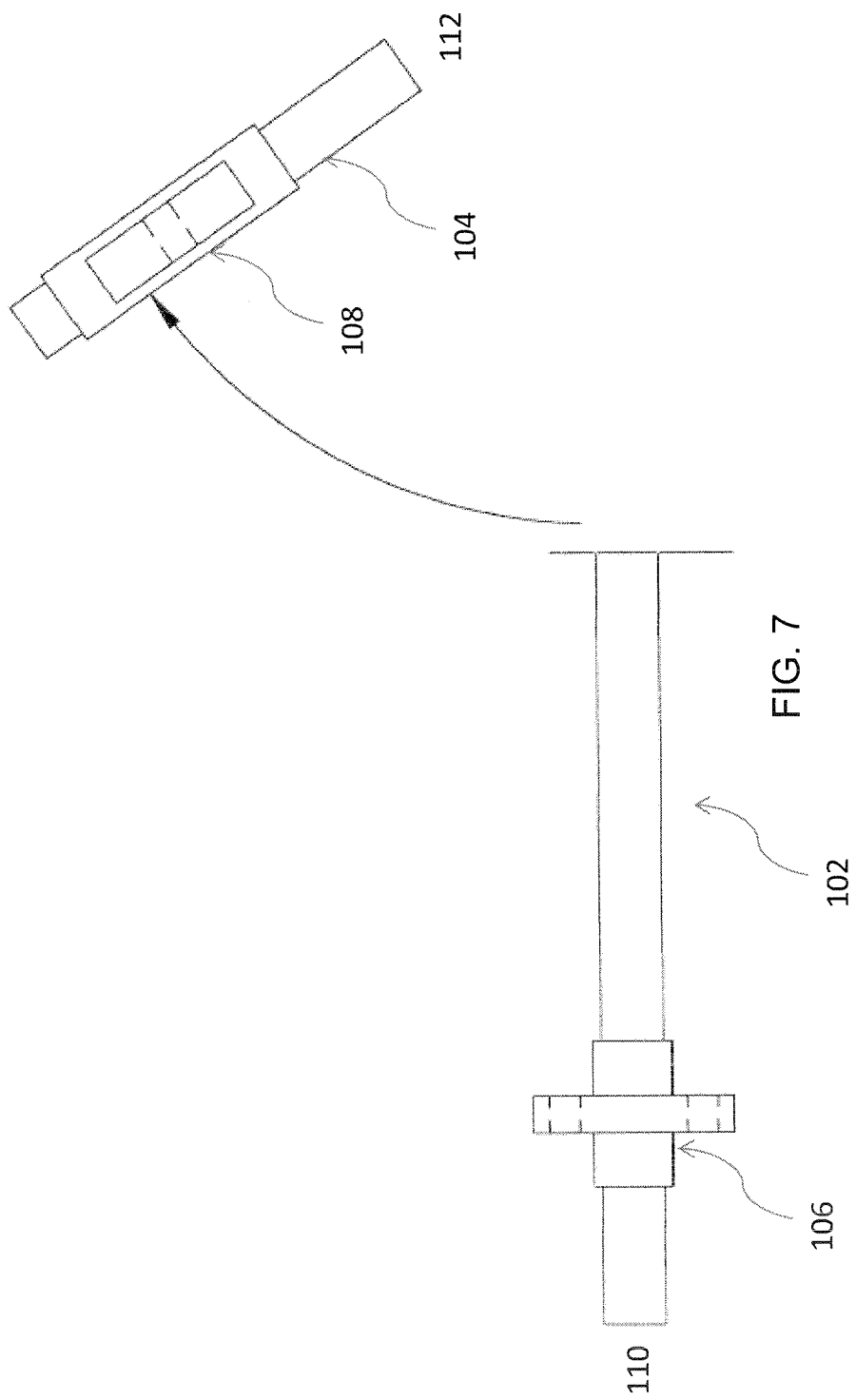

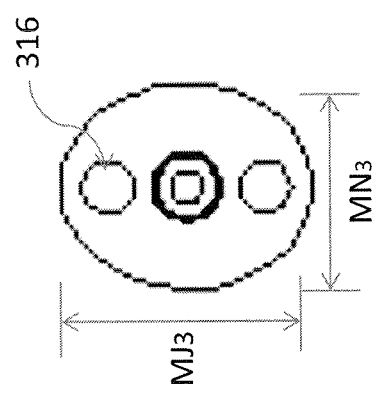
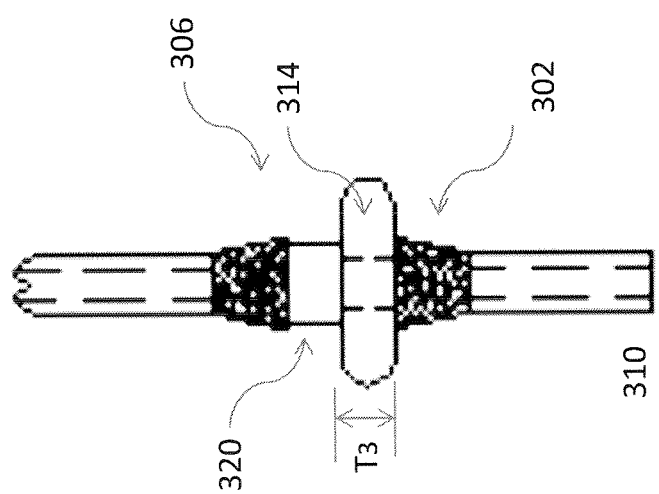
FIG. 11B
FIG. 11A

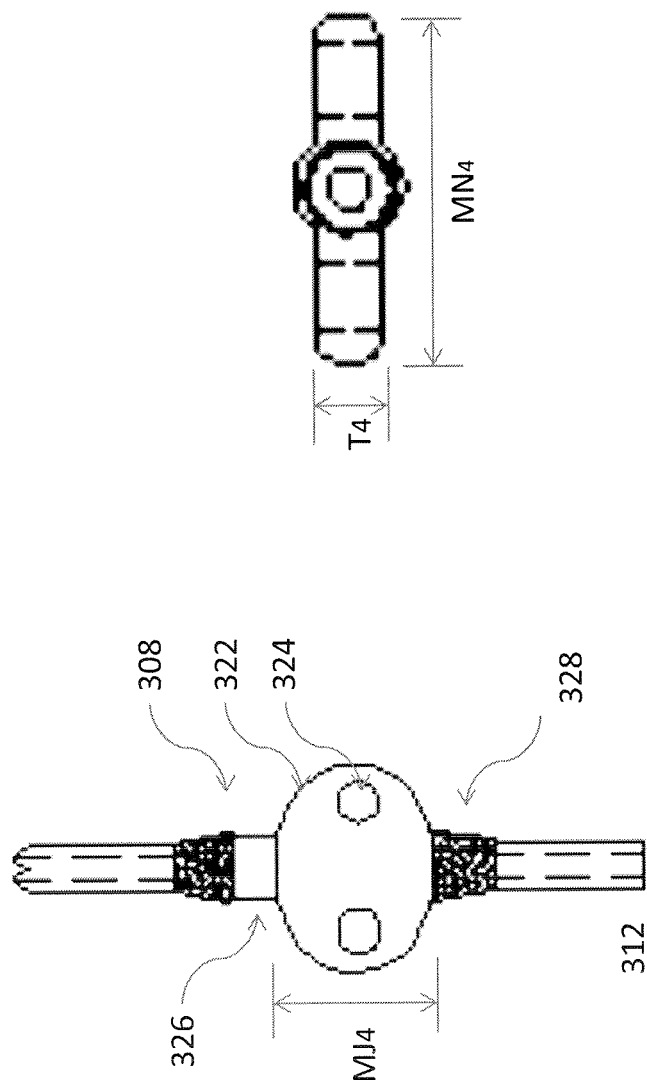

IMPLANT DEVICE FOR USE IN SALIVARY GLAND DUCT

CROSS REFERENCE TO RELATED APPLICATIONS

This application is a continuation-in-part of U.S. application Ser. No. 13/180,187 filed on Jul. 11, 2011, which claims priority to U.S. provisional application Ser. No. 61/362,985, filed on Jul. 9, 2010 and to U.S. provisional application Ser. No. 61/423,968 filed on Dec. 16, 2010. This application also claims priority to U.S. provisional application Ser. No. 61/653,825 filed on May 31, 2012. The entirety of each of these applications is incorporated herein by reference.

FIELD OF THE INVENTION

The instant invention is directed to a medical implant device. More particularly, the instant invention is directed to a medical implant device used in the treatment of salivary duct channels.

BACKGROUND OF THE INVENTION

Salivary glands are found in and around a person's mouth and throat. The major salivary glands are the parotid, submandibular, and sublingual glands. These glands provide the needed saliva to assist in food chewing and early digestion of certain carbohydrates. Saliva is drained through salivary ducts into the oral cavity. The parotid duct connects from the parotid gland to near the upper teeth, the submandibular duct connects from the submandibular gland to under the tongue, and the duct of Rivinus connects from the sublingual gland to the floor of the mouth on the sublingual fold.

Among the different salivary gland problems encountered, obstruction to the flow of saliva via the salivary gland duct may be the most common. This may be caused by the formation of stones, which can become lodged in the duct. Thus, the saliva produced in the salivary gland cannot exit the ductal system and enter the oral cavity. The lack of saliva flow contributes to dry mouth disorder and can cause swelling of the salivary gland, leading to pain and possible infection.

Other problems may include the development of kinks in the salivary gland ducts, stenosis (i.e., constriction or narrowing) of the salivary gland ducts, or generally, other structural or structurally related defects associated with the salivary glands and/or salivary gland ducts.

It is therefore advantageous to facilitate the integrity of the salivary ducts and their respective glands, especially when their integrity is compromised, and to treat glands rather than remove them.

SUMMARY OF THE INVENTION

It is an object of the invention to provide an implant device that is operable, among other functions, to maintain, repair, and/or restore the structure and functionality of salivary gland ducts, and that is simple to remove once this is accomplished.

According to certain embodiments, an implant device for placement within a salivary gland duct having a first end adjacent to a parotid gland and a second end adjacent to a submandibular gland is provided. The implant device comprises an elongate body having a lumen, and a first and a second plate offset from the proximal end of the elongate body. The first plate is located on one side of the elongate body and the second plate is located on the other side of the elongate body. The first plate includes a first and a second hole operable to suture the first plate to a location adjacent the parotid gland. The second plate includes a first and a second hole operable to suture the second plate to a location adjacent the submandibular gland. Upon placement of the implant device within the salivary gland duct, saliva flows postoperatively in the salivary duct along the outside of the implant device wall, or in some embodiments, through the lumen of the implant device.

According to other embodiments, a method for implanting an implant device within a salivary gland duct having a first end adjacent a parotid gland and a second end adjacent a submandibular gland is provided. The implant device comprises an elongate body having a lumen, and a first and a second plate offset from the proximal end of the elongate body. The first plate is located on one side of the elongate body and the second plate is located on the other side of the elongate body. The first plate includes a first and a second hole operable to suture the first plate to a location adjacent the parotid gland. The second plate includes a first and a second hole operable to suture the second plate to a location adjacent the submandibular gland. Upon placement of the implant device within the salivary gland duct, saliva flows postoperatively in the salivary duct along the outside of the implant device wall, or in some embodiments, through the lumen of the implant device.

In certain embodiments, the implant device is a stent. In some embodiments, the implant device is a cannula.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which:

FIGS. 2A-C illustrate one end of a salivary gland duct implant device according to embodiments of the present invention;

FIGS. 3A-C illustrate one end of a salivary gland duct implant device according to embodiments of the present invention;

FIGS. 6A-C illustrate one end of a salivary gland duct implant device according to embodiments of the present invention;

FIG. 7 illustrates an undesired end being truncated in an exemplary embodiment of a salivary gland duct implant device according to embodiments of the present invention;

FIGS. 11A-B illustrate one end of a salivary gland duct implant device according to embodiments of the present invention; and FIGS. 12A-B illustrate one end of a salivary gland duct implant device according to embodiments of the present invention.

DETAILED DESCRIPTION OF THE INVENTION

The instant invention will now be described more fully hereinafter with reference to the accompanying drawings, in which embodiments of the invention are shown. This invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art.

The following embodiments of the present invention describe an implant device that is operable for use in association with the salivary ducts of a patient. Particularly, such an implant device is placed within a salivary duct over a predefined period of time (e.g., two to four weeks) in order to restore the physical and/or functional integrity of the duct by, for example, facilitating the flow of saliva.

Figure 1:
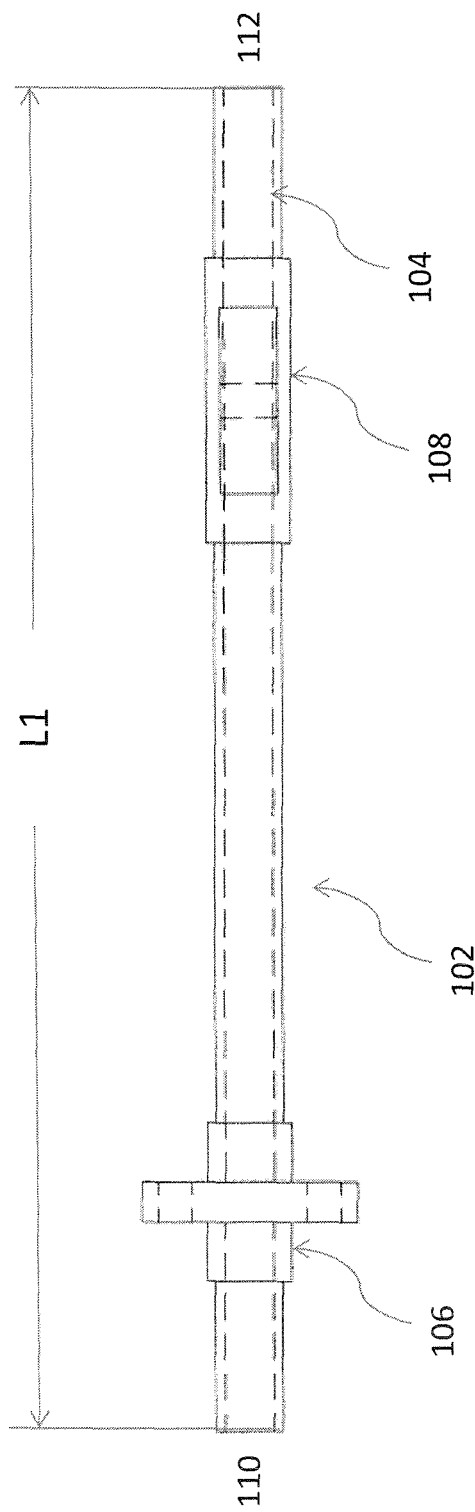
FIG. 1 illustrates an exemplary embodiment of a salivary gland duct implant device from a side view perspective according to embodiments of the present invention.
Figure 4:
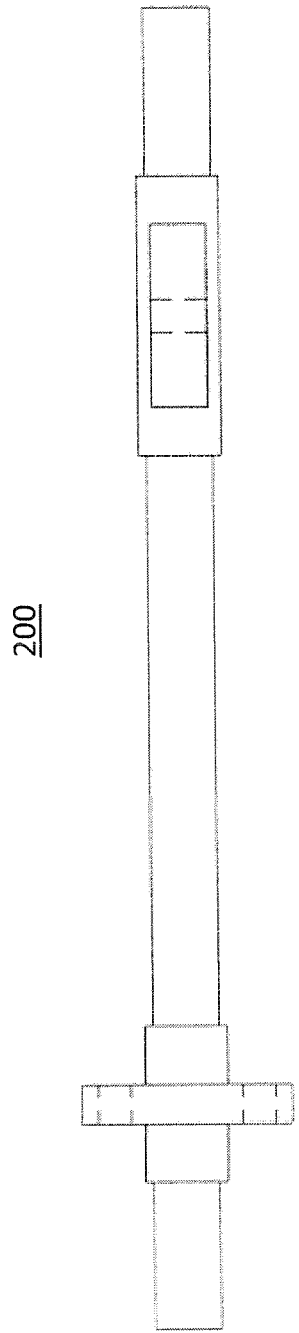
FIG. 4 illustrates an exemplary embodiment of a salivary gland duct implant device from a side view perspective according to embodiments of the present invention.
Figure 5C:
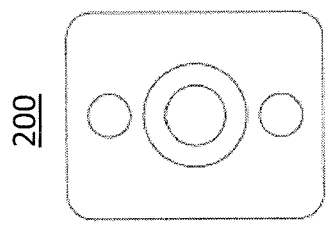
FIGS. 5A-C illustrate one end of a salivary gland duct implant device according to embodiments of the present invention.
Figure 5B:
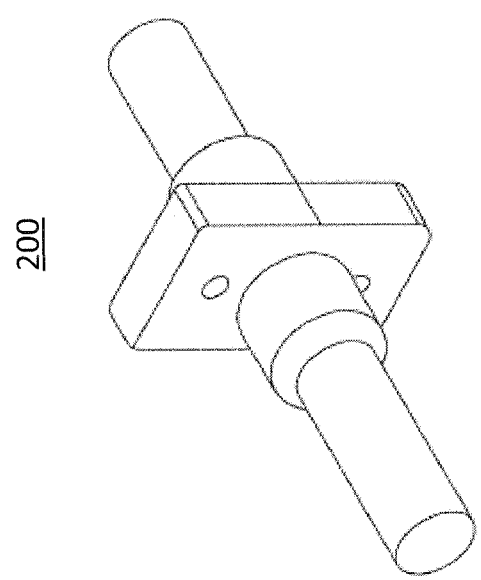
Figure 5A:
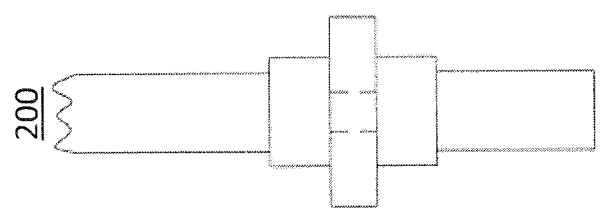

In accordance with certain embodiments, as illustrated in FIG. 1, a suitable implant device 102 may comprise an elongate body 104 having a length of about 50 to about 90 millimeters (mm). The elongate body 104 of the illustrated implant device 102 typically may have a length L1 of about 79 mm and a substantially uniform circular cross section. Both the inner and outer surfaces of the elongate body 104 may be coated with Paralyene or any other suitable coating material that facilitates the insertion of the implant device 102 within a duct (not shown), prevents tissue build-up or growth (i.e., non-biointegratable) during the implantation period, and prevents adhesion to the duct walls, thereby allowing for ease of removal and for free flow of saliva in the salivary duct along the outside of the implant device wall. The implant device's elongate body 104 may be produced from a soft/flexible material such as, but not limited to, silicone rubber, which upon insertion within the salivary duct, provides a requisite degree of comfort for the patient. Alternatively, the implant device's elongate body 104 may be produced from a flexible, but firm, material, such as a thermoplastic elastomer, for example, Pebax.

As shown in FIG. 1, the implant device 102 may be comprised of suturing regions 106 and 108 that are offset from the proximal end 110 and the distal end 112 of the elongate body 104, respectively. FIG. 2A is a side view of the proximal end 110 of implant device 102, which comprises suturing region 106. Suturing region 106 may include a suture plate 114, which may extend on either side of the elongate body 104, and offset from the proximal end 110 by a distance $O_1$. The suture plate 114 may include suturing holes 116, as shown in FIGS. 2B and 2C, for suturing the proximal end portion 110 of the implant device 102 to an area of the parotid gland that may be approximately adjacent to the end of the salivary duct from which saliva flows. Although suturing holes 116 may be located within plate 114, an alternative or additional hole (not shown) may be provided within plate 114. In terms of dimensions, the width Wt of the suturing plate may be about 4 mm, while the length of the plate $L_1$ may be approximately 10 mm, and the thickness of the plate $T_1$ may be approximately 1 mm, as shown in FIGS. 2B and 2C, for example. The length of offset $O_1$ from the proximal end 110 may be about 5 mm. The diameter of suturing holes 116 may be approximately 1 mm.

The suturing region 106 may optionally comprise a gripping portion 118 on which the suture plate 114 may be positioned. Gripping portion 118 may be used to maintain the integrity of the papilla, and to aid in holding the implant device 102 in place inside the duct. Gripping portion 118 may be co-molded with the suture plate 114 or may be a separate component that may be attached to the implant device 102.

The suture plate 114 may be offset from the proximal end 110 of the implant device 102 in order to position the implant device's proximal end 110 away from the end of the salivary duct. Since one of the primary functions of the implant device is to be a conduit for the flow of saliva, the extension of the implant device 102 into the oral cavity caused by suture plate 114 being offset from the proximal end 110 may allow the saliva to flow more effectively into the oral cavity.

FIG. 3A is a side view of the distal end 112 of implant device 102, which comprises suturing region 108. Suturing region 108 may include a suture plate 122, which may extend on either side of the elongate body 104, and offset from the distal end 112 by a distance $O_2$. The suture plate 122 may include suturing holes 124, as shown in FIG. 3B, for suturing the distal end portion 112 of the implant device 102 to an area of the submandibular gland. Although suturing holes 124 may be located within plate 122, an alternative or additional hole (not shown) may be provided within plate 122. In terms of dimensions, the width $W_2$ of the suturing plate may be about 4 mm, while the length of the plate $L_2$ may be approximately 5 mm, and the thickness of the plate $T_2$ may be approximately 1 mm, as shown in FIGS. 3B and 3C, for example. The length of offset $O_2$ from the distal end 112 may be about 5 mm. The diameter of suturing holes 124 may be approximately 1 mm.

The suturing region 108 may optionally comprise a gripping portion 126 on which the suture plate 122 may be positioned. Gripping portion 126 may be co-molded with the suture plate 122 or may be a separate component that may be attached to the implant device 102.

It should be noted, however, that suturing plates 114 and 122 may be removed so that the proximal or distal end 110 or 112 of the implant device 102 may be inserted into the salivary duct opening located at the salivary gland. The use of suturing region 108 and its respective suture plate 122 may provide an alternative means for placement of the implant device 102 when inserting the implant device 102 from the oral cavity end of the salivary duct may be impractical or impossible. This procedure involving the use of suturing region 108 may, however, require some surgical cutting in order to access the salivary duct via the salivary gland.

FIGS. 2C and 3C depict end views of the implant device 102 illustrated in FIGS. 2B and 3B, respectively. Accordingly, FIG. 2C illustrates a substantially rectangular cross-section associated with the elongate body 104 of the implant device 102. Although, the elongate body 104 of the implant device 102 preferably has a circular cross-section, an elliptical or alternatively shaped cross-section may be contemplated based on the physical repair or remedy needed for the particular duct receiving the implant device 102. As shown, elongate body 104 may include a lumen (i.e., the bore of the tube shaped elongate body 104) that may have a diameter $D_1$ of approximately 0.50 mm. The lumen may, however, include any diameter in the range of about 0.25 to about 1.5 mm. The overall total diameter $D_2$ of the elongate body 104 may be about 2.0 mm. The elongate body 104 may, however, include any overall total diameter in the range of about 0.60 to about 2.0 mm The lumen may provide a conduit for the flow saliva within the implant device 102 or along the outside of the implant device wall when the implant device 102 may be placed or implanted within the salivary duct. $D_3$, as shown in FIGS. 2C and 3C, may be the outer diameter of the gripping portions 118 and 126, respectively.

It should be noted, however, that the inner diameter of the through hole in the elongate body 104 (lumen), suture plates 114, 122, as well as the gripping portions 118, 126 may be the same or different. For example, FIG. 2A illustrates the through hole in the elongate body 104 (lumen), suture plate 114, and the gripping portions 118 as being different from each other. However, FIG. 3A illustrates the through hole in the elongate body 104 (lumen), suture plate 122, and the gripping portions 126 as being the same. $D_1$, $D_2$, and $D_3$, may have diameters in the range of about 0.25 mm to about 2.0 mm. The elongate body 104 (lumen), suture plates 114, 122, as well as the gripping portions 118, 126 may be transparent or translucent, for example.

Once inserted, the instant implant device 102 allows saliva to flow postoperatively in the salivary duct along the outside of the implant device wall. The implant device 102 may relieve dry mouth in patients undergoing, for example, chemotherapy. The implant device 102 can also be used to treat salivary gland disorders such as: sialolithisis, salivary gland swelling, kinks, and stones.

According to some embodiments, the suture plates 114, 122 may be in two different planes, as illustrated in FIG. 1, for example. The plate 122 that is in the same plane as the tube is used to suture the implant device 102 to the floor of the mouth or the submandibular gland, and the plate 114 that is 90 degrees to the tube is used to suture to the cheek of the patient or the parotid gland, for example. The physician may be able to out off a segment towards one end of the implant device 102 in order to eliminate the plate that will not be used, such as that shown in FIG. 7, for example. The physician may also be able to fashion the length of the implant device to fit the needs of the procedure.

According to certain embodiments, the implant device 200 may have a solid body. As shown in FIGS. 4 to 6C, for example, the implant device 200 may use a solid rod as the elongate body, instead of a translucent or transparent body as shown in FIGS. 1 to 3C, for example. Similarly, the suture plates as well as the gripping portions may be made of a solid material, instead of being translucent or transparent.

In further embodiments, the implant device 300 may comprise suture plates that are circular or elliptical, which may be less intrusive and can reduce the possibility of irritation to the interior of the mouth as compared to suture plates that are rectangular. As shown in FIGS. 10A to 10E, for example, the implant device 300 may comprise suturing regions 306 and 308 that are offset from the proximal end 310 and the distal end 312 of the elongate body 304, respectively. Suturing region 306 may include an elliptical suture plate 314 that may include suturing holes 316. In terms of dimensions, the major axis $MJ_3$ of the suturing plate may be about 10 mm, the minor axis $MN_3$ of the plate may be approximately 4 mm, and the thickness of the plate $T_3$ may be approximately 1 mm. The diameter of suturing holes 316 may be approximately 1 mm. Suturing region 308 may include an elliptical suture plate 322 that may include suturing holes 324. Regarding dimensions, the major axis $MJ_4$ of the suturing plate may be about 5 mm, the minor axis $MN_4$ of the plate may be approximately 4 mm, and the thickness of the plate $T_4$ may be approximately 1 mm. The diameter of suturing holes 324 may be approximately 1 mm.

In certain embodiments, the suturing region may comprise a shoulder adjacent to the suture plate on each side of the plate. In some embodiments, a shoulder may be absent from one of the sides of the suture plate in order to reduce profile and thereby reduce the possibility of irritation. This is depicted in FIGS. 11A and 12A, in which there is only one shoulder 320 adjacent to the suture plate 314 and only one shoulder 326 adjacent to the suture plate 322.

In some embodiments, the suturing region may be bordered by fillets. This is illustrated in FIGS. 11A and 12A, in which there are fillets 302 on each side of the suturing region 306, and fillets 328 on each side of the suturing region 308. The fillet 302, 328 comprises a curved shape that provides a smoothed surface between the shoulder 320, 326 or the suture plate 314, 322 and the elongate body 104. The fillet 302, 328 can reduce possible irritation inside the patient's mouth by smoothing the surface of the implant device. The fillet 302, 328 may be made out of silicone.

The suture plates 114, 122 may be molded out of soft, flexible, and suitably strong silicone rubber. The plates 114, 122 will then fit and conform to the anatomy at that particular area of the mouth, causing minimal discomfort to the patient. The suture plates 114, 122 may comprise two suture holes as described in the earlier paragraphs, providing the means to anchor the implant device 102 with a mattress suture, which gives a very stable and secure positioning.

In certain embodiments, the implant device is a stent. In other embodiments, the implant device is a cannula.

According to certain embodiments, the invention is a method for implanting the implant device 102, 200 within a salivary gland duct. According to the method, a suture is made with a double stitch that forms a loop about the tissue on both sides of a wound. A surgical stitch in which the suture 102, 200 is passed back and forth through both edges of a wound so that the needle is reinserted each time on the side of exit and passes through to the side of insertion. The suture for parotid placement and submandibular placement is illustrated in FIGS. 8 and 9, for example.

During clinical studies, implant device would, occasionally, extrude due to the failure of the sutures prior to the desired 7- to 14-day rehabilitation period. However, the method of suturing and the plate design according to the present invention have prevented unwanted extrusion. As shown in FIGS. 8 and 9, for example, the suture plate 114, 122 orientations and flexibility make it possible for the fixture to be discreet and comfortable for the patient. A flexible, but firm material, may be used in the main body of the implant device 102, 200, such as thermoplastic elastomer, Pebax, which may provide ease of insertion and be comfortable for patient. The flexible, but firm material also enables the ease of removal. Alternatively, the material may be, for example, silicone rubber.

Figure 8:
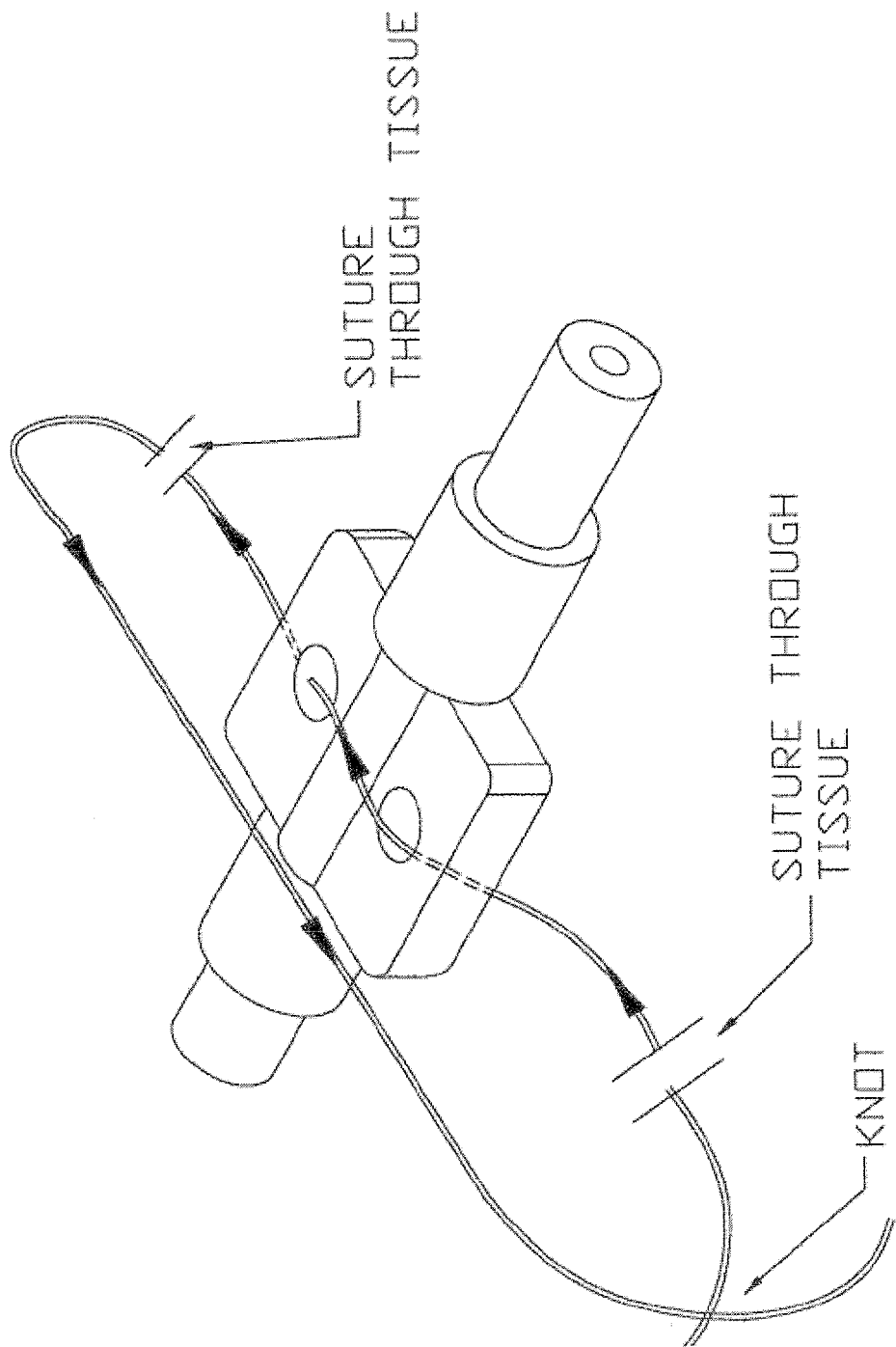
FIG. 8 illustrates an exemplary embodiment of a salivary gland duct implant device from a perspective view according to embodiments of the present invention.
Figure 9:
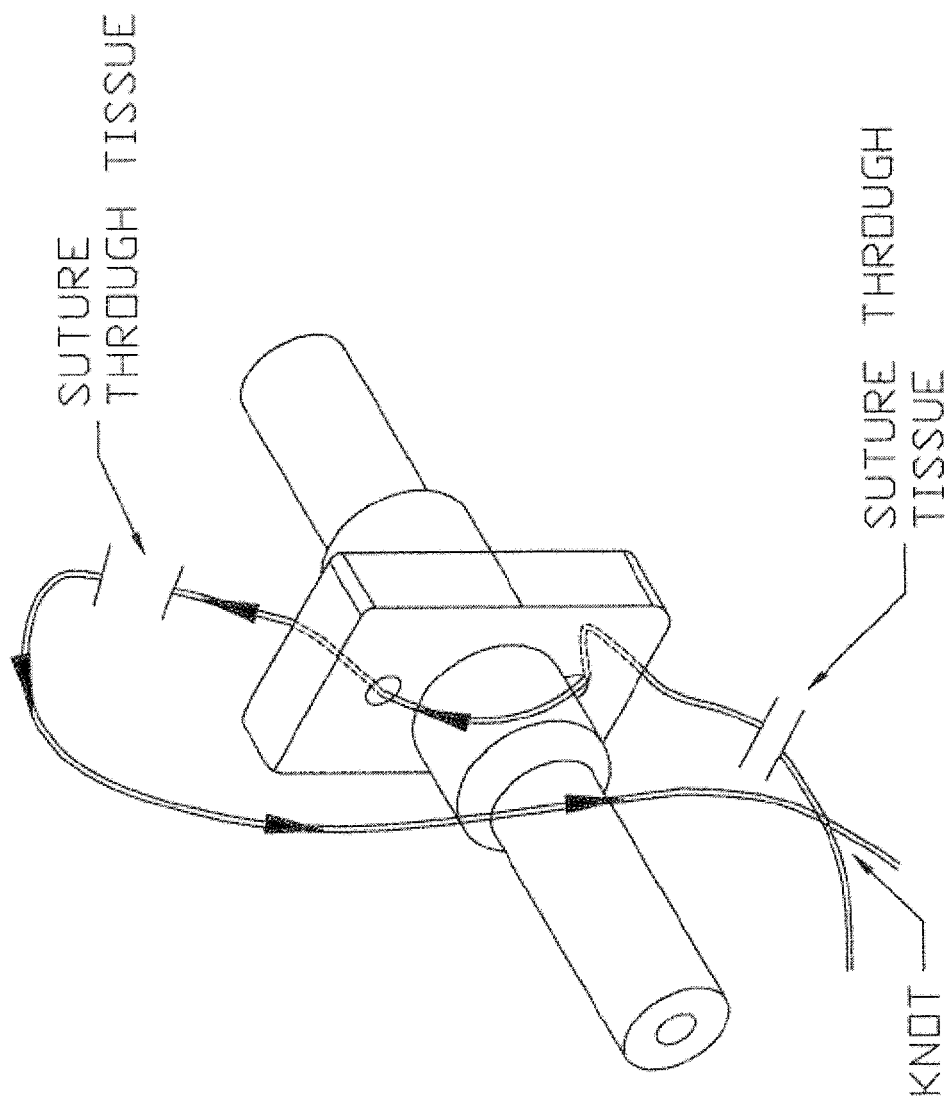
FIG. 9 illustrates an exemplary embodiment of a salivary gland duct implant device from a perspective view according to embodiments of the present invention.
Figure 10:
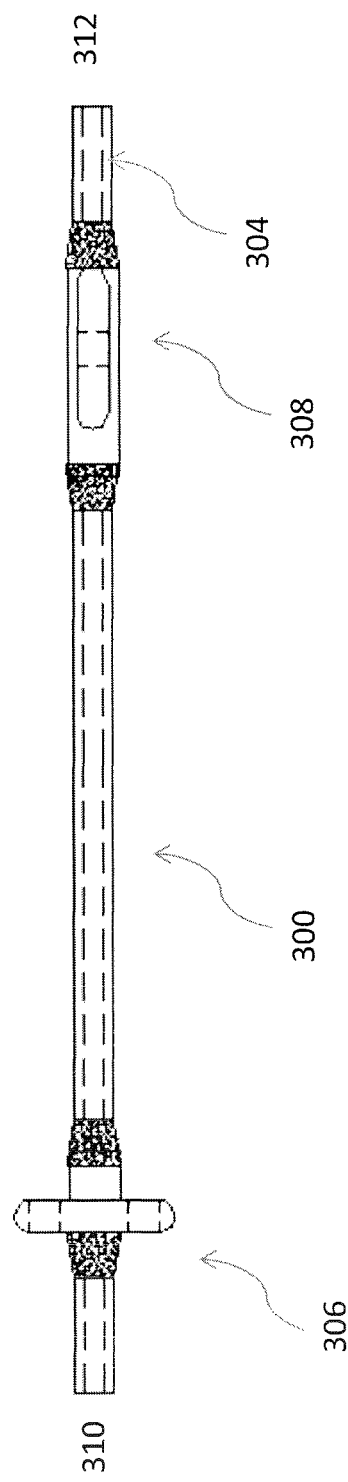
FIG. 10 illustrates an exemplary embodiment of a salivary gland duct implant device from aside view perspective according to embodiments of the present invention.

As depicted in FIGS. 8 and 9, the shoulders on either side of the suture plates 114, 122 serve a number of purposes, including contributing to holding the implant device 102, 200 in place, thereby increasing the strength of the connection of the plates to the tube, and serving the purpose of maintaining the integrity of the papilla.

The implant device 102, 200 according to the present invention can be sold in a kit with a balloon catheter, for example. The balloon catheter can be used to remove the stone from the salivary duct. The implant device can then be inserted into the duct as a means of maintaining the duct post-procedure.

In certain embodiments, a flexible guide wire can be used to guide the implant device of the present invention into position.

Although embodiments of the present invention and modifications thereof have been described in detail herein, it is to be understood that this invention is not limited to these precise embodiments and modifications, and that other modifications and variations may be effected by one skilled in the art without departing from the spirit and scope of the invention as defined by the appended claims.

What is claimed is:

1. An implant device for placement within a salivary gland duct, the implant device comprising:
   an elongate body having a lumen;
   a first plate offset from a proximal end of the elongate body, the first plate located on one side of the elongate body, the first plate being substantially perpendicular to, and extending across, a plane of the elongate body;
   a second plate offset from a distal end of the elongate body, the second plate located on the other side of the elongate body, the second plate being substantially in the plane of, and extending across, the elongate body and substantially perpendicular to the first plate;
   a first fillet adjacent the first plate, the first fillet having a curved shape and disposed on the elongate body; and
   a second fillet adjacent the second plate, the second fillet having a curved shape and disposed on the elongate body,
   wherein the first plate and the second plate each have at least two holes located on opposite sides of the elongate body,
   wherein upon the placement of the implant device within the salivary gland duct, saliva flows through or along the outside wall of the implant device.

2. The implant device according to claim 1, wherein the first plate is configured to suture the implant device to a parotid gland.

3. The implant device according to claim 1, wherein the second plate is configured to suture the implant device to a submandibular gland.

4. The implant device according to claim 1, wherein the elongate body comprises a substantially uniform cross section of a substantially circular shape.

5. The implant device according to claim 1, wherein the implant device is made from silicone rubber or an elastomeric material.

6. The implant device according to claim 1, wherein the elongate body comprises a coating for facilitating the insertion and removal of the implant device with respect to the salivary duct, and inhibiting biological tissue build up around the implant device.

7. The implant device according to claim 6, wherein the coating comprises Paralyene.

8. The implant device according to claim 1, wherein the lumen has a diameter in the range of about 0.25 to about 1.50 millimeters.

9. The implant device according to claim 1, wherein the elongate body comprises a length in the range of about 50 to about 90 millimeters.

10. The implant device according to claim 1, wherein the elongate body comprises an overall diameter in the range of about 0.60 to about 2.0 millimeters.

11. The implant device according to claim 1, wherein the offset from the proximal end of the elongate body is about 2 to about 10 millimeters.

12. The implant device according to claim 1, wherein the offset from the distal end of the elongate body is about 2 to about 10 millimeters.

13. The implant device according to claim 1, wherein the first plate and the second plate are made from silicone rubber or an elastomeric material.

14. The implant device according to claim 1, wherein the first plate and the second plate are rectangular- or elliptical-shaped.

15. The implant device according to claim 1, wherein the implant device is a stent or a cannula.

16. The implant device of claim 1, comprising:
    a first shoulder adjacent the first plate, the first shoulder disposed on the elongate body; and
    a second shoulder adjacent the second plate, the second shoulder disposed on the elongate body.

17. The implant device of claim 16, wherein the first and second shoulders are concentric with the elongate body.

18. The implant device of claim 17, comprising:
    another first shoulder adjacent the first plate, the another first shoulder disposed on the elongate body and adjacent a side of the first plate opposite the first shoulder; and
    another second shoulder adjacent the second plate, the another second shoulder disposed on the elongate body and adjacent a side of the second plate opposite the first shoulder.

19. The implant device of claim 16, wherein at least one of the first and second fillets is next to one of the first and second shoulders.

20. A method of implanting an implant device within a salivary gland duct, the implant device comprising an elongate body having a lumen;
    a first plate offset from a proximal end of the elongate body, the first plate located on one side of the elongate body, the first plate being substantially perpendicular to, and extending across, a plane of the elongate body;
    a second plate offset from a distal end of the elongate body, the second plate located on the other side of the elongate body, the second plate being substantially in the plane of, and extending across, the elongate body and substantially perpendicular to the first plate, the first plate and the second plate each having at least two holes located on opposite sides of the elongate body;
    a first fillet adjacent the first plate, the first fillet having a curved shape and disposed on the elongate body; and
    a second fillet adjacent the second plate, the second fillet having a curved shape and disposed on the elongate body,
    the method comprising the steps of:
    placing of the implant device within the salivary gland duct;
    suturing the first plate to a parotid gland through the diametrically opposed holes; and
    suturing the second plate to a submandibular gland through the diametrically opposed holes such that saliva flows through or along the outside wall of the implant device.

* * * * *